United States Patent
Cohen et al.

(10) Patent No.: US 7,402,593 B2
(45) Date of Patent: Jul. 22, 2008

(54) MONOHYDRATED SODIUM SALT OF S-TENATOPRAZOLE AND THE USE THEREOF IN THERAPY

(75) Inventors: Avraham Cohen, Tel Aviv (IL); François Schutze, Saint-Nom-la-Bretèche (FR); Suzy Charbit, Créteil (FR); Frédéric Martinet, Paris (FR); Hervé Ficheux, Nogent-sur-Marne (FR); Michel Homerin, Courcouronnes (FR)

(73) Assignee: Sidem Pharma, Luxembourg (LU)

( * ) Notice: Subject to any disclaimer, the term of this patent is extended or adjusted under 35 U.S.C. 154(b) by 0 days.

(21) Appl. No.: 10/561,844

(22) PCT Filed: Jun. 17, 2005

(86) PCT No.: PCT/FR2005/001528

§ 371 (c)(1), (2), (4) Date: Jan. 5, 2007

(87) PCT Pub. No.: WO2006/005853

PCT Pub. Date: Jan. 19, 2006

(65) Prior Publication Data

US 2007/0179176 A1 Aug. 2, 2007

(30) Foreign Application Priority Data

Jun. 17, 2004 (FR) .................................. 04 06617

(51) Int. Cl.
| | |
|---|---|
| A01N 43/42 | (2006.01) |
| A61K 31/44 | (2006.01) |
| C07D 471/02 | (2006.01) |
| C07D 491/02 | (2006.01) |
| C07D 498/02 | (2006.01) |
| C07D 513/02 | (2006.01) |
| C07D 515/02 | (2006.01) |

(52) U.S. Cl. ...................................... 514/303; 546/118

(58) Field of Classification Search ................. 514/303; 546/118

See application file for complete search history.

(56) References Cited

U.S. PATENT DOCUMENTS

| 5,753,265 A | * | 5/1998 | Bergstrand et al. .......... 424/474 |
|---|---|---|---|
| 7,034,038 B2 | | 4/2006 | Cohen et al. |
| 2006/0194832 A1 | | 8/2006 | Cohen et al. |
| 2006/0241136 A1 | | 10/2006 | Schutze et al. |
| 2006/0287284 A1 | | 12/2006 | Schutze et al. |
| 2007/0066659 A1 | | 3/2007 | Schutze et al. |

FOREIGN PATENT DOCUMENTS

| CN | 1453278 | * 11/2003 |
|---|---|---|
| EP | 0 254 588 | 1/1988 |
| FR | 2 848 555 | 6/2004 |
| WO | 2004/074285 | 9/2004 |

OTHER PUBLICATIONS

Bunpei Kakinoki et al. "General Pharmacological Properties of the New Proton Pump Inhibitor (±)-5-Methoxy-2-[[(4-methoxy-3,5-dimethylpyrid-2-yl)methyl]sulfinyl]-1H-imidazo[4,5-b]pyridine", vol. 21, No. 3, 1999, pp. 179-187.
International Search Reported dated Nov. 30, 2005.

* cited by examiner

*Primary Examiner*—D. Margaret Seaman
*Assistant Examiner*—Niloofar Rahmani
(74) *Attorney, Agent, or Firm*—Crowell & Moring LLP

(57) ABSTRACT

The present invention relates to S-tenatoprazole monohydrated sodium salt, represented by the following formula

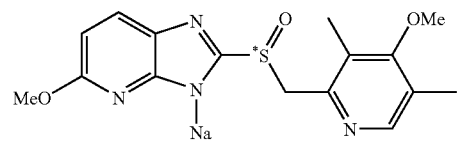

and the use thereof in therapy for the treatment of digestive diseases.

18 Claims, No Drawings

MONOHYDRATED SODIUM SALT OF S-TENATOPRAZOLE AND THE USE THEREOF IN THERAPY

BACKGROUND OF THE INVENTION

1. Field of the Invention

The present invention concerns a tenatoprazole salt, and more particularly a monohydrated salt of the (−) enantiomer of tenatoprazole, or S-tenatoprazole, a method for its preparation as well as its use in human or veterinary therapeutics, namely as proton pump inhibitor (PPI) to treat gastro-oesophageal reflux, digestive bleeding and dyspepsia.

2. Description of the Related Art

Different sulfoxide derivatives, and notably pyridinyl-methyl-sulfinyl benzimidazoles, have been described in the literature for their therapeutic properties allowing for their use as medicinal products presenting proton pump inhibiting properties to be envisaged, that is to say medicinal products which inhibit the secretion of gastric acid and are useful in the treatment of gastric and duodenal ulcers.

Omeprazole, or 5-methoxy-2-[[(4-methoxy-3,5-dimethyl-2-pyridyl)methyl]sulfinyl]-1H-benzimidazole described in patent EP 005.129, is one of the first known derivatives of the series of PPIs, possessing gastric acid secretion inhibiting properties, and is widely used as an anti-ulcerative in human therapeutics. Rabeprazole, pantoprazole and lansoprazole can also be found among the other known derivatives of pyridinyl-methyl-sulfinyl-benzimidazoles with a similar structure.

Tenatoprazole, or 5-methoxy-2-[ [(4-methoxy-3,5-dimethyl-2-pyridyl)methyl]sulfinyl]imidazo[4,5-b]pyridine, is described in Patent No. EP 254.588. It also belongs to the group of drugs classified under the name of "proton pump inhibitors" (PPIs), and can be used for the treatment of conditions such as gastro-oesophageal reflux, digestive bleeding and dyspepsia.

These sulfoxides have an asymmetry at the level of the sulphur atom, and can therefore generally take the form of a mixture (racemic mixture or racemate) of two enantiomers or of one or the other enantiomer. These enantiomers can classically be used under the form of salts, such as magnesium, potassium or sodium salts, which are generally easier to handle than the bases.

Patent EP 652.872 describes the magnesium salt of esomeprazole, (−) enantiomer of omeprazole, as well as a method for its preparation, the separation of the diastereo-isomers and the solvolysis in an alkaline solution. The enantioselective preparation of the (−) enantiomer of omeprazole or of its sodium salts, by oxidation of the corresponding sulphide by a hydroperoxide in the presence of a titanium complex and a chiral ligand is described in U.S. Pat. No. 5,948,789. The method described in this patent produces a mixture enriched in one or the other of the (−) and (+) enantiomers, according to the ligand used.

Different formulations have been proposed in order to improve the properties or the activity of PPIs. In the case of omeprazole, for example, PCT application WO 01.28558 describes a stable liquid formulation obtained by forming the sodium or potassium salts in situ in solution in polyethylene glycol, by action of a hydroxide on omeprazole. The medicinal product thus formulated can be used in the usual indications of PPIs.

SUMMARY OF THE INVENTION

Recent studies have shown that unexpectedly and unlike all the other PPIs (such as, for example, omeprazole or lansoprazole), tenatoprazole possesses a remarkably long duration of action which is the result of a longer half-life in plasma (approximately seven times longer). Indeed, clinical data have shown that tenatoprazole induces a degree of symptom relief and healing of gastric lesions which is superior to those achieved by other PPIs, and which allows for its effective use in the treatment of diseases and conditions such as, for example, atypical and oesophageal symptoms of gastro-oesophageal reflux, digestive bleeding and dyspepsia, as indicated above. Moreover, it was demonstrated that each of the (+) or (−), or "R" and "S" configuration enantiomers, respectively, contributes differently to the properties of tenatoprazole and the S-tenatoprazole exhibits significantly different pharmacokinetic properties from those of the racemate and of the other enantiomer. S-tenatoprazole is described in French patent application No 2.848.555 published on 18 Jun. 2004.

Studies conducted by the applicant have shown that the monohydrated sodium salt of S-tenatoprazole exhibits unexpected properties which differentiate it from S-tenatoprazole itself, and from other PPIs, and more particularly an excellent solubility which makes it easier to set into its pharmaceutical form and which significantly improves its absorption and the therapeutic efficacy of the medicinal product in which it is contained.

Thus, an object of the present invention is the monohydrated sodium salt of S-tenatoprazole, and the use thereof in human or veterinary therapeutics.

Another object of the present invention is a solution concentrated in monohydrated sodium salt of S-tenatoprazole, and more particularly an aqueous solution at a concentration in monohydrated sodium salt of S-tenatoprazole higher than or equal to 50 g/l, and preferably higher than or equal to 100 g/l.

The present invention also relates to a pharmaceutical composition comprising the monohydrated sodium salt of S-tenatoprazole, substantially free from the (+) enantiomer of R-tenatoprazole, associated to one or more pharmaceutically acceptable excipients and substrates.

A further object of the present invention is the use of the monohydrated sodium salt of S-tenatoprazole in the manufacture of a medicinal product to treat digestive diseases and conditions where the inhibition of acid secretion must be effective and prolonged to treat, for example, the symptoms and lesions of gastro-oesophageal reflux disease, or digestive bleeding refractory to other PPIs, and especially treat these diseases and conditions in patients receiving multiple drug therapy.

A further object of the present invention is the use of the monohydrated sodium salt of S-tenatoprazole in the manufacture of a drug with a significantly improved rate of healing as well as an increase in the speed of normalization of histological changes of the gastric lesions in animals or humans, which result in a strong decrease in relapses.

The present invention also concerns the use of the monohydrated sodium salt of S-tenatoprazole in the manufacture of a medicinal product with improved pharmacokinetic properties that would allow taking a single dose of medication per day in relevant indications, as indicated hereafter, and particularly in the eradication of *Helicobacter pylori* during the treatment of duodenal ulcer, condition which usually requires two doses (morning and evening) of other PPIs.

Another object of the present invention is an enantioselective method of preparation of the monohydrated sodium salt of S-tenatoprazole, producing the (−) enantiomer salt with a good purity and a satisfactory yield.

DETAILED DESCRIPTION

The monohydrated sodium salt of S-tenatoprazole can be prepared by enantioselective oxidation of a sulphide of the following general formula (I)

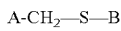

where A is a substituted pyridyl nucleus and B an imidazopyridyl nucleus, using an oxidising agent in the presence of a vanadium based catalyst and a chiral ligand in a specific sulphide solvent and a specific ligand solvent, according to the method of preparation described in patent application FR 2.863.611, followed by salification by sodium hydroxide.

In the above-mentioned general formula (I), the pyridyl group A is a 4-methoxy-3,5-dimethyl-2-pyridyl group and B represents a 4-methoxy-imidazo[4,5-b]pyridyl group.

The oxidizing agent used in the method is preferably a peroxide, for example hydrogen peroxide. According to an advantageous method of implementation, highly concentrated hydrogen peroxide is preferably used, higher than 30% for example.

According to the invention, the catalyst may be selected from V oxo-vanadium complex catalysts, and more preferably vanadium acetylacetonate. Such catalysts are commercially available.

A ligand such as a Schiff base derived from a substituted salicylic aldehyde and from a chiral amino-alcohol is preferably used in combination with the catalyst. The choice of the ligand allows for a selective orientation of the reaction towards the desired enantiomer. Thus, the use of 2,4-di-tert-butyl-6-[1-R-hydroxymethyl-2-methyl-propylimino)-methyl]-phenol allows for a selective orientation of the oxidation of 5-methoxy-2-[[4-methoxy-3,5-dimethyl-2-pyridyl)methyl]thio]imidazo[4,5-b]pyridine, in order to obtain S-tenatoprazole selectively.

The reaction may be carried out in a solvent, and preferably in a mixture of solvents, in neutral or weakly basic medium, by choosing a specific sulphide solvent and a specific ligand solvent among the group constituted by methanol, tetrahydrofuran, methylene chloride, acetonitrile, acetone and N-methyl-pyrrolidone or toluene, alone or as a mixture. The base possibly used may be a tertiary amine such as pyridine, di-isopropylethylamine or triethylamine. The oxidation reaction is easily conducted at low or room temperature.

It is particularly advantageous to use the vanadium based catalyst and the ligand in acetonitrile solution, while the sulphide is dissolved in a chlorinated solvent such as dichloromethane, and to combine both solutions before letting the oxidant operate.

More particularly, the oxidation of the sulphide of formula (I) allows for the (−) enantiomer to be obtained, that is, S-tenatoprazole, under good purity and yield conditions by using a vanadium base catalyst associated with a ligand constituted by 2,4-di-tert-butyl-6-[1-R-hydroxymethyl-2-methyl-propylimino)-methyl]-phenol in acetonitrile solution, while sulphide is dissolved in dichloromethane. Under operating conditions, the ligand and the metallic catalyst form an asymmetric complex where the metal is oxidized by the oxidizing agent.

The oxidation reaction can easily be conducted at low or room temperature, preferably at a temperature comprised between 0 and 10° C. so as to facilitate the enantioselectivity.

The sulphide of formula (I) used as starting material is a known product that can be prepared according to several methods described in literature, and for example, according to the methods described in Patents No. EP 254.588 and EP 103.553.

S-tenatoprazole is thus obtained, that is the laevogyre enantiomer of tenatoprazole, and can be represented by the following general formula:

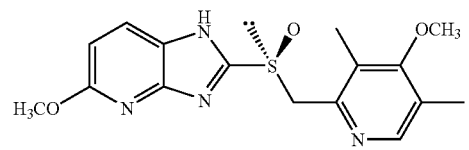

The (−) enantiomer of tenatoprazole, or S-tenatoprazole, corresponds to (−)-5-methoxy-2-[[(4-methoxy-3,5-dimethyl-2-pyridyl)methyl]sulfinyl]imidazo[4,5-b]pyridine, or (−) tenatoprazole. This form can be determined by optical rotation measurements according to standard techniques. Thus, in dimethylformamide and acetonitrile, the angle of optical rotation of (−) tenatoprazole is levorotatory, and its melting point is 130° C. (decomposition).

According to an alternative, S-tenatoprazole can also be obtained in a pure optical form from the racemic mixture by well known techniques, using any appropriate method of separation, for example by preparative column chromatography, such as chiral chromatography or high performance liquid chromatography (HPLC). The principle of the chiral chromatography method is based on the difference in affinity existing between (+) and (−) enantiomers and the chiral selector of the stationary phase.

The racemic mixture used as starting material can be obtained using known processes, for example according to the method described in Patent No EP 254.588. Thus, it can be prepared using an oxidizing agent, such as perbenzoic acid, to treat the corresponding sulphide arising from the condensation of a thiol and a pyridine, preferably in the presence of a base such as potassium hydroxide in an appropriate solvent, for example ethanol, under heating. The racemic mixture thus obtained may be separated by HPLC as indicated above.

S-tenatoprazole, obtained according to one or the other above-mentioned methods is then salified in order to obtain a salt with the following formula (II):

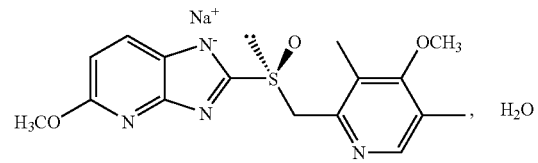

In the above formula, the sodium atom may be fixed on the second nitrogen of the imidazopyridyl nucleus close to the sulfoxide group, both isomers being in equilibrium.

The salification is conducted by action of sodium hydroxide on S-tenatoprazole at a temperature comprised between 50 and 70° C., preferably at about 60° C., in a solvent such as water, chloroform, DMSO or a protic solvent, for example methanol or ethanol, then by precipitating the salt obtained after elimination of the solvent. The reaction is preferably conducted under inert atmospheric conditions (nitrogen or argon).

The salt is precipitated according to standard techniques using a solvent miscible with water, where the salt is sparingly soluble, for example a ketone such as acetone and methyl ethyl ketone. The monohydrated salt may be identified by its physico-chemical properties, as indicated further down.

The racemic tenatoprazole salt may be prepared using the same method in order to perform comparative tests, notably solubility tests, with the sodium salt of the isomer.

The thermal analysis measurements and the X-ray diffraction allowed for the characterisation of the structure of the monohydrated sodium salt of S-tenatoprazole, and showed the existence of the monohydrated sodium salt of S-tenatoprazole, which is significantly different from the other forms such as the anhydrous or amorphous forms and the solvates.

Thus, other crystallised phases of the sodium salt may be produced by modifying the crystallisation conditions (temperature, isolation mode), and the solvents (polarity modulation). For example, the use of dioxane leads to the formation of a perfectly crystallised and characterised solvate of the isomer sodium salt. Nonetheless, the presence of dioxane in the crystalline mesh seems inappropriate for use in pharmaceutics.

The amorphous form, the preparation of which is described in Example 6 here-after, is uncrystallised, instable and difficult to use in pharmaceutical compositions.

Another crystallised phase which can be obtained is the anhydrous sodium salt, described in Example 4 here-after. However, the DVS (Dynamic Vapour Sorption) study revealed the instable nature of this polymorph under usual conditions of relative humidity, leading to the deliquescence of the product. Because of this unstable character, this polymorph is unsuitable for use in pharmaceutics, in particular in usual formulations.

The thermo gravimetric profile of the sodium salt shows that a variable fraction of water (comprised between 1 and 4%) desorbs at low temperature (from 30° C. to 50° C.) and constitutes a labile and reversible fraction of water. The dehydration of a molecule of water can be observed around 130° C. (about 5% of loss of mass). The monohydrated sodium salt was also characterised by DVS (Dynamic Vapour Sorption).

As indicated above, the monohydrated sodium salt of tenatoprazole exhibits excellent solubility properties in water and the major solvents. Thus, the solubility in water ranges from about 140 to 150 g/l at 25° C., and from 240 to 290 g/l at 45° C., which is considerably higher than that of the sodium salt of racemic tenatoprazole (about 18 to 19 g/l), whereas those of racemic tenatoprazole and S-tenatoprazole are lower than 1 g/l.

This result is totally unexpected compared to the solubility of the other well known proton pump inhibitors.

Thus, the monohydrated sodium salt of S-tenatoprazole allows for the preparation of solutions highly concentrated in active medicinal principle, with concentrations higher than 50 g/l, and preferably higher than 100 g/l. For comparison, the racemate sodium salt does not allow for concentrations higher than 19 g/l to be obtained at room temperature.

The monohydrated sodium salt of S-Tenatoprazole exhibits good stability characteristics under normal temperature, pressure and hygrometry conditions. According to environmental and storage conditions, the stoichiometric ratio between the sodium salt and water may evolve and be comprised between 1 and 2. Thus, the water contents corresponding to the sesquihydrated and dihydrated forms may be detected. However, this phenomenon is reversible. The present application relates altogether to the monohydrated sodium salt and to the sesquihydrated and dihydrated sodium salts of S-Tenatoprazole.

A study in the dog showed that the use of the monohydrated sodium salt of S-tenatoprazole allows for a much higher bioavailability to be obtained than with S-tenatoprazole, that is to say a higher concentration (C max) as well as a greater exposure, as measured by the area under the curve of the concentrations according to time (AUC t), for the same dose. Besides, the faster release (Tmax 1.3 hours for monohydrated sodium salt versus 2.5 hours for S-tenatoprazole) allows for therapeutic concentrations to be reached much faster, and thus for the onset of action of the medicinal product to be improved, therefore favouring the possibility of on-demand therapy.

These results are gathered in the following table comparing the monohydrated sodium salt (salt) to basic (free acid) S-tenatoprazole.

| dose | T max h | C max ng·mL$^{-1}$ | AUC t ng·h·mL$^{-1}$ |
|---|---|---|---|
| 100 mg/kg (salt) | 1.3 | 183 021 | 822 785 |
| 100 mg/kg (free acid) | 2.5 | 104 751 | 434 017 |

The improvement allows for the administered dose to be reduced by a factor of 1.5 to 2, for a comparable exposure. The result is that for a same dose of active principle, the therapeutic efficacy is doubled by the use of the monohydrated sodium salt according to the present invention.

A pharmacokinetic study on dog (n=6) conducted over 4 weeks, comparing the effects of racemic tenatoprazole and of the monohydrated sodium salt of S-tenatoprazole evidenced the original properties of the latter.

The results are gathered in the table below.

| dose | T max h | C max ng·L$^{-1}$ | AUC t ng·h·mL$^{-1}$ |
|---|---|---|---|
| 5 mg/kg (salt) | 0.5 | 15 648 | 42 208 |
| 25 mg/kg (salt) | 0.5 | 77 548 | 148 633 |
| 50 mg/kg (salt) | 0.7 | 125 883 | 323 942 |
| 50 mg/kg Racemic tenatoprazole | 1.5 | 50 179 | 155 592 |

In this table, the abbreviations have the usual meaning, that is to say that Cmax stands for the maximum plasmatic concentration, Tmax for the time (duration) during which the maximum plasmatic concentration is observed and AUCt for the area under the curve of the plasmatic concentration.

These results were measured on the 28$^{th}$ day of administration.

In this study, the monohydrated sodium salt of S-tenatoprazole, at the doses of 5 mg/kg of weight, 25 mg/kg and 50 mg/kg, and racemic tenatoprazole at the dose of 50 mg/kg, were administered under the form of encapsulated powder.

These results show that the monohydrated sodium salt has a more rapid action (shorter Tmax) than the racemate, whichever the dose used, and provides values of AUC and Cmax that are twice as high for the same dose.

These results were confirmed by a clinical study in man (n=6) during which the patients were successively administered a single dose of: a) capsules of monohydrated sodium salt of S-Tenatoprazole under gastro-resistant form according to a usual technique, b) the same monohydrated sodium salt in powder (non gastro-protected), and c) non salified racemic tenatoprazole, also under the form of capsules containing non gastro-protected powder.

The results obtained are provided in the table below.

| Formulation | Cmax ng·mL$^{-1}$ | AUCinf ng·h·mL$^{-1}$ | T½ h |
|---|---|---|---|
| a) | 5340 | 50844 | 7.81 |
| b) | 3199 | 31223 | 8.36 |
| c) | 2488 | 21058 | 7.29 |

$AUC_{inf}$ is the area under the curve of the plasmatic concentration calculated to the infinite, with extrapolation of the final phase, and $T_{1/2}$ is the plasmatic half-life.

We can therefore observe that the monohydrated sodium salt of tenatoprazole, even non gastro-protected, brings a significant improvement of the parameters.

These results therefore confirm those of the animal studies and demonstrate that the monohydrated sodium salt of S-tenatoprazole allows for an increase in the exposition (AUC) of about 50% compared to the racemic tenatoprazole. The same goes for the maximum concentration (Cmax).

Thus, the monohydrated sodium salt of S-tenatoprazole not only possesses different pharmacokinetic properties, but also allows for the diminution of the dose by about one third for a similar efficacy.

In the treatment of the conditions listed here-after, the monohydrated sodium salt of S-tenatoprazole can be administered in standard forms adapted to the method of administration chosen, for example via the oral or parenteral routes, and preferably via the oral or intravenous routes. In particular, the excellent solubility of the monohydrated sodium salt of S-tenatoprazole allows for it to be administered via the intravenous route and thus to ensure the maximal bioavailability of the medicinal product.

The usual formulations of the pharmaceutical technique may be used, for example, it is possible to use tablet or capsule formulations containing the monohydrated sodium salt of S-tenatoprazole as the active principle, or oral solutions or emulsions or solutions for parenteral administration containing the tenatoprazole sodium salt with a standard, pharmaceutically-acceptable substrate.

According to an advantageous form, gastro-resistant granules may also be prepared which can be inserted in a capsule or incorporated in a tablet formulation. The gastro-resistant granules may be prepared by applying a layer of appropriate polymer, such as a cellulosic or methacrylic polymer, for example Eudragit®, on a neutral nucleus carrying a layer containing the active principle.

According to another form particularly adapted to the solubility characteristics of the monohydrated sodium salt of S-tenatoprazole, the nucleus consists in a mixture of a diluent, for example a cellulosic diluent, a disintegrating agent, and the monohydrated sodium salt of S-tenatoprazole, this nucleus being covered with an enteric film, for example an acetophtalate or methacrylate film.

The disintegrating agent may be a cellulosic polymer, such as cellulose carboxymethyl polymer, for example sodium croscarmellose. The diluent used is preferably an excipient for direct compression, which prevents the use of a wet granulation step. Eudragit® may be used for the enteric coating.

Such a formulation is designed to release the active principle in less than about 5 minutes at pH 6.8, that is to say in the duodenum, after going through the stomach at a more acidic pH.

According to another characteristic, the monohydrated sodium salt has a relative stability in acid medium, which differentiates it from the other proton pump inhibitors. This property allows for the use of the monohydrated sodium salt of S-tenatoprazole in formulations without enteric coating, according to the desired treatment mode. Such formulations present optimised pharmacokinetics and constitute an ideal compromise between the release of the active substance, its immediate action and its relatively small degradation in the stomach. They therefore provide for an additional alternative to the above-described enteric-coated formulations for the practitioner.

The monohydrated sodium salt of tenatoprazole may be used in the manufacture of a medicinal product to treat digestive diseases and conditions where the inhibition of acid secretion must be effective and prolonged to treat, for example, the symptoms and lesions of gastro-oesophageal reflux disease, or digestive bleeding refractory to other PPIs.

The dosage is determined by the practitioner as a function of the patient's state and the severity of the condition. It is generally comprised between 10 and 120 mg, preferably between 10 and 80 mg, more preferably between 15 and 40 mg, of active principle per day.

The excellent solubility of the monohydrated sodium salt of S-tenatoprazole allows for a better absorption of the active principle, and therefore a better bioavailability.

In particular, the bioavailability of the active principle under a form for oral administration, such as tablets or capsules, is close to that obtained by intravenous administration, which leads to the high effectiveness of the product.

The preparation of the monohydrated sodium salt of S-tenatoprazole is described here-after, as well as its original properties, in order to illustrate the present invention, without limiting its scope.

EXAMPLE 1

Preparation of (S)-(−)-tenatoprazole

3 L of methylene chloride and then 360 g of 5-methoxy-2-[[4-methoxy-3,5-dimethyl-2-pyridyl)methyl]thio]imidazo[4,5-b]-pyridine are added in a 5 L flask. The mixture is left under stirring for 30 minutes at room temperature.

700 mL of acetonitrile, 5.22 g of 2,4-di-tert-butyl-6-[1-R-hydroxymethyl-2-methyl-propylimino)-methyl]-phenol, and 2.90 g of vanadyl acetylacetonate are dropped one after the other in a 2 L flask. The mixture is kept under stirring at room temperature. After stirring for 30 min, this solution is added to the previous one.

135 mL of hydrogen peroxide at 30% are added to this mixture under stirring for 20 hours at room temperature. After separation of the aqueous phase, the organic phase is washed twice with water, then dried and concentrated under reduced pressure. 283 g of the desired enantiomer are obtained, with an enantiomeric excess higher than 80% (75% yield). Two successive recrystallisations are performed in a methanol/water or DMF/ethyl acetate mixture and the enantiomer is obtained with an enantiomeric excess higher than 99%.

T$_F$: 127.5° C.

[α]$_D$: −182 ((c 0.1, DMF)

UV spectrum (methanol-water): λ$_{max}$: 272 nm (ε=6180), 315 nm (ε=24877).

Infra-red (KBr): 3006, 1581, 1436, 1364, 1262 cm$^{-1}$.

NMR $^{13}$C (KOH, reference: sodium 3-(trimethylsilyl)-1-propane-sulfonate) δ (ppm): 13.2; 15.0; 56.6; 60.8; 62.6; 107.2; 129.5; 130.4; 131.9; 135.1; 150.5; 151.4; 156.9; 160.7; 163.0; 166.6.

MNR $^1$H (DMSO d$_6$, reference: TMS) δ (ppm): 2.20 (s, 6H), 3.70 (s, 3H), 3.91 (s, 3H), 4.69-4.85 (m, 2H), 6.80 (d, J 8.5 Hz, 1H), 7.99 (d, J 8.5 Hz, 1H), 8.16 (s, H), 13.92 (s, 1H).

EXAMPLE 2

Preparation of the Monohydrated Sodium salt of (S)-(−)-tenatoprazole 1.0 mL of water and 0.6 mL of sodium hydroxide in aqueous solution (5M) are dropped under slow agitation at room temperature in a 50 mL flask equipped with a stirrer, a temperature sensor and a condenser, and containing 1.0 g of S-(−)-tenatoprazole obtained as described in Example 1.

The reaction mixture is heated to 60° C. and maintained under stirring for 2.5 hours. An oily liquid is obtained which is cooled down at room temperature before the solvent is eliminated under reduced pressure at 40° C. in a rotatory evaporator. After 6 mL of acetone are added under stirring, the pale yellow product precipitates and is collected by filtration on sintered glass and rinsed in 2.0 mL of acetone or diethyl ether.

After drying at 40° C. under reduced pressure for 20 hours, 1.1 g of monohydrated sodium salt of S-tenatoprazole are obtained with a yield higher than 90%.

The monohydrated sodium salt was characterised by thermal analysis and by X-ray diffraction at variable temperature.

Melting point TF: 235° C. (capillaries method: Büchi B545 apparatus)

Water content: 5.8% (Karl Fischer)

Enantiomeric excess: higher than 99% (chiral chromatography).

MNR $^1$H (DMSO d$_6$, reference: TMS) δ (ppm): 8.23 (1H, s); 7.70 (1H, d, J=8.4 Hz); 6.37 (1H, d, J=8.4 Hz); 4.73 (1H, d, J=12.9 Hz); 4.37 (1H , d, J=12.9 Hz); 3.82 (3H, s); 3.70 (3H, s); 2.22 (3H, s); 2.21 (3H, s).

Thermogravimetric Analysis:

The thermogravimetric analysis is performed using a Netzsch SCA 409 PC/PG thermobalance. The measurements are made in an aluminium crucible between 20° C. and 150° C. with a heating up speed of 2°/min under nitrogen pressure.

The thermogravimetric profile reveals three successive steps:

between 10 and 40° C.: evaporation, loss of 1.35% of water, between 90 and 130° C.: dehydration, loss of 4.65% (desorption of a molecule of water), between 160 and 230° C.: degradation, loss of 9.42%.

Diagram of the X-Ray Diffraction at Variable Temperature:

The analysis was conducted with a Siemens D5005 diffractometer (copper anticathode, voltage of 40 kV, intensity of 30 mA, room temperature, measurement range from 3 to 30°, increments between each measurement of 0.04°, measurement time by 4 s).

The measurement data are provided in the table below:

| Monohydrated sodium salt of S-tenatoprazole | | | |
|---|---|---|---|
| Angle 2-Theta ° | value of d (Angstrom) | Intensity (Count) | Intensity (%) |
| 5.965 | 14.80418 | 508 | 2.9 |
| 6.585 | 13.41257 | 17768 | 100 |
| 10.389 | 8.50818 | 446 | 2.5 |
| 12.891 | 6.8615 | 1352 | 7.6 |
| 13.264 | 6.66969 | 670 | 3.8 |
| 15.341 | 5.77085 | 676 | 3.8 |
| 17.294 | 5.12337 | 507 | 2.9 |
| 19.247 | 4.60779 | 444 | 2.5 |
| 19.896 | 4.45871 | 1763 | 9.9 |
| 20.925 | 4.24174 | 740 | 4.2 |
| 21.6 | 4.11076 | 627 | 3.5 |
| 21.824 | 4.06909 | 609 | 3.4 |
| 22.316 | 3.98048 | 484 | 2.7 |
| 22.885 | 3.88278 | 1106 | 6.2 |
| 23.457 | 3.78939 | 2731 | 15.4 |
| 25.479 | 3.49302 | 637 | 3.6 |
| 26.151 | 3.40479 | 864 | 4.9 |
| 26.636 | 3.34392 | 709 | 4 |
| 27.506 | 3.2401 | 380 | 2.1 |
| 28.32 | 3.14875 | 396 | 2.2 |
| 28.526 | 3.12648 | 467 | 2.6 |
| 29.708 | 3.00467 | 570 | 3.2 |

The monohydrated sodium salt was also characterised by DVS (Dynamic Vapour Sorption).

The recordings were performed with a SMS apparatus (Surface Measurement System) with the following characteristics:

| | |
|---|---|
| maximum capacity: | 1.5 g |
| sensitivity: | 1.5 μg |
| temperature range: | 5-48° C. |
| humidity range: | 0-98% RH |
| precision: | 1% RH |

This technique allows for the aptitude of a product to hydrate, dehydrate, solvate and desolvate to be determined by measuring the uptake or the loss of mass according to the controlled atmosphere in terms of water or solvent content at an average temperature.

The results are provided in the following table:

| Residual humidity % | Water content (p/p %) | |
|---|---|---|
| | Absorption | Desorption |
| 20 | 3.75 | 4.40 |
| 40 | 4.45 | 4.52 |
| 60 | 4.62 | 4.63 |
| 80 | 4.71 | 4.71 |

These results show that the stoichiometry of the monohydrated phase is maintained from 20 to 80% of relative humidity without any deliquescence phenomenon appearing, contrarily to the anhydrous phase (see Example 3). This outlines the excellent stability of the monohydrated sodium salt in presence of humidity.

Under these conditions of strong relative humidity, higher than 80%, the stoichiometry of the sodium salt of S-tenatoprazole may evolve, the number of molecules of water being comprised between 1 and 2. This form, which is also within the scope of the present invention, exhibits an X-ray diffraction at variable temperature diagram similar to the one presented above:

| Monohydrated sodium salt of S-tenatoprazole + Second partial hydration | | | |
|---|---|---|---|
| Angle 2-Theta ° | value of d (Angstrom) | Intensity (Count) | Intensity (%) |
| 5.921 | 14.91531 | 497 | 3 |
| 6.586 | 13.40893 | 16710 | 100 |
| 12.867 | 6.87461 | 1252 | 7.5 |
| 13.275 | 6.6642 | 675 | 4 |
| 17.269 | 5.13084 | 501 | 3 |
| 19.203 | 4.61808 | 590 | 3.5 |
| 19.941 | 4.44894 | 1967 | 11.8 |
| 20.999 | 4.22702 | 946 | 5.7 |
| 23.509 | 3.78109 | 1685 | 10.1 |
| 25.511 | 3.48876 | 457 | 2.7 |
| 26.262 | 3.39065 | 650 | 3.9 |
| 26.727 | 3.33264 | 729 | 4.4 |
| 27.544 | 3.23569 | 707 | 4.2 |
| 28.602 | 3.11837 | 471 | 2.8 |
| 29.765 | 2.99907 | 675 | 4 |

EXAMPLE 3

Preparation of the Monohydrated Sodium salt of S-(−)-tenatoprazole

According to an alternative of the process of Example 2, the monohydrated sodium salt is prepared as follows.

25 mL of chloroform are dropped in a 250 mL three-neck distilling flask equipped with a stirrer, a refrigerant and a temperature sensor. 10 g of S-tenatoprazole obtained as described in Example 1 are added and maintained under stirring until solubilisation in chloroform. The mixture is cooled down on an ice/water bed at 4-5° C., before 150 mL of acetone are added. The mixture is then maintained at 4-5° C.

3.85 g of soda lye (30%) are added under stirring whilst maintaining the temperature at 4-5° C., before the reaction medium is let to return to room temperature (20-25° C.) while maintained under stirring for 16 hours. The start of a precipitation can be observed after one hour of contact.

The reaction medium is cooled down to a temperature of 4-5° C. on an ice bed and maintained under stirring for 4 hours. After filtration of the reaction medium on sintered glass, the powder is collected and rinsed with 15 mL of previously frozen acetone. After vacuum-drying in an oven at 60° C. for one night, about 10 g of product are obtained under the form of monohydrated sodium salt of S-tenatoprazole with a yield higher than 90%.

The characteristics of the salt are identical to those of Example 2.

COMPARATIVE EXAMPLE 4

Preparation of the Anhydrous Sodium Salt of S-(−)-tenatoprazole

Based on the S-(−)-tenatoprazole from Example 1, and using the method described in Example 2, sodium hydroxide in aqueous solution is caused to react on S-tenatoprazole at 60° C. to obtain an oily liquid which is taken up in acetone once the water has been eliminated under reduced pressure, and it has been rinsed and dried. The product obtained is set in suspension in a mixture of methanol/acetonitrile (25/75) at 50° C., then cooled down to 5° C. to form a white precipitate which is collected by filtration, working in an environment protected from humidity.

Crystallisation yield: 85%.

The X-ray diffraction at variable temperature diagram performed with a Brüker D5000 type apparatus (copper anticathode, 40 V, 30 mA), provides the following results:

| Angle (°) 2-Theta | Value of d | Intensity |
|---|---|---|
| 6.6 | 13.3 | 100 |
| 9.5 | 9.3 | 1 |
| 14.3 | 6.2 | 2 |
| 15.1 | 5.9 | 2 |
| 15.9 | 5.6 | 2 |
| 17.4 | 5.1 | 1 |
| 18.3 | 4.8 | 2 |
| 19.9 | 4.5 | 8 |
| 20.9 | 4.2 | 2 |
| 21.4 | 4.1 | 2 |
| 22.1 | 4.0 | 1 |
| 22.7 | 3.9 | 2 |
| 22.9 | 3.9 | 2 |
| 23.9 | 3.7 | 2 |
| 24.9 | 3.6 | 1 |
| 26.4 | 3.4 | 2 |
| 27.2 | 3.3 | 2 |
| 27.6 | 3.2 | 1 |
| 29.5 | 3.0 | 2 |
| 30.5 | 2.9 | 1 |
| 36.3 | 2.5 | 1 |

DVS characteristics (recorded under the same conditions as in Example 2):

| Residual humidity % | Water uptake (p/p %) | |
|---|---|---|
| | Absorption | Desorption |
| 0 | 0.00 | 3.41 |
| 20 | 0.12 | 12.09 |
| 40 | 0.25 | 16.45 |
| 60 | 0.65 | 19.14 |
| 80 | 24.86 | 24.86 |

It can be noted that the anhydrous phase becomes irreversibly deliquescent beyond 60% of relative humidity (residual humidity), contrarily to the monohydrated phase.

COMPARATIVE EXAMPLE 5

Preparation of the 1,4-dioxane Solvate/Sodium Salt of S-(−)-tenatoprazole

Based on the S-(−)-tenatoprazole from Example 1, sodium hydroxide in aqueous solution is caused to react on S-tenatoprazole at 60° C. according to the method described in Example 2, in order to obtain an oily liquid which is taken up in acetone once the water has been eliminated under reduced pressure and it has been rinsed and dried.

The product thus obtained is set in suspension in a sufficient volume of 1,4-dioxane at 25° C. (1 g for about 100 mL of dioxane). The suspension is concentrated slowly at room temperature for 48 hours and is then filtered to obtain the 1,4-dioxane solvate/sodium salt (1/1) under the form of white powder.

Thermogravimetric Analysis:

The thermogravimetric analysis is performed under the conditions described in Example 2.

First, the evaporation is observed.

Second, the desolvation of 1,4-dioxane occurs from 70 to 100° C. The loss of mass in the $3^{rd}$ and $4^{th}$ steps justifies the stoichiometry of the 1/1 solvate.

X-Ray Diffraction at Variable Temperature Diagram:

The X-ray diffraction at variable temperature is performed with a Brüker D5000 type apparatus (copper anticathode, 40 V, 30 mA) and the results are presented below:

| Angle (°) 2-Theta | Value of d | Intensity |
|---|---|---|
| 7.7 | 11.5 | 12 |
| 11.5 | 7.7 | 39 |
| 12.6 | 7.0 | 100 |
| 13.1 | 6.8 | 9 |
| 13.3 | 6.6 | 8 |
| 14.2 | 6.2 | 8 |
| 14.6 | 6.1 | 5 |
| 15.2 | 5.8 | 17 |
| 15.5 | 5.7 | 20 |
| 17.5 | 5.1 | 17 |
| 18.2 | 4.9 | 15 |
| 18.8 | 4.7 | 7 |
| 20.4 | 4.4 | 6 |
| 23.3 | 3.8 | 57 |
| 24.1 | 3.7 | 36 |
| 25.0 | 3.6 | 5 |
| 26.5 | 3.4 | 7 |
| 26.8 | 3.3 | 14 |
| 34.7 | 2.6 | 12 |
| 35.3 | 2.5 | 13 |
| 36.0 | 2.5 | 8 |

COMPARATIVE EXAMPLE 6

Preparation of the Amorphous Sodium Salt of S-(−)-tenatoprazole 1.0 mL of water and 0.6 mL of sodium hydroxide in aqueous solution (5M) are dropped at room temperature into a 50 mL flask containing 1.0 g of S-(−)-tenatoprazole obtained as indicated in Example 1.

The reaction medium is brought to 60° C. and maintained under stirring for 2.5 hours. An oily liquid is obtained which is cooled down at room temperature, before the solvent is eliminated under reduced pressure at 40° C. After 5 mL of water are added under stirring, the amorphous salt precipitates and is collected by filtration. The X-ray diffraction spectrum does not present any diffraction bands.

The invention claimed is:

1. The monohydrated sodium salt of S-tenatoprazole represented by the general formula (II):

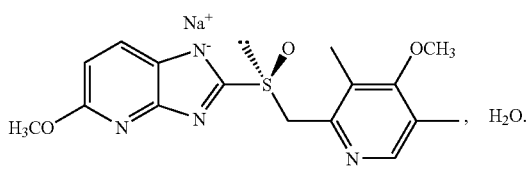

2. A concentrated solution of monohydrated sodium salt of S-tenatoprazole according to claim 1, wherein the concentration in monohydrated salt is higher than or equal to 50 g/l.

3. A concentrated solution according to claim 2, wherein the concentration in monohydrated salt is higher than or equal to 100 g/l.

4. A pharmaceutical composition comprising the monohydrated sodium salt of S-tenatoprazole according to claim 1, associated to one or more pharmaceutically acceptable excipients.

5. A composition according to claim 4, wherein it is under the form of unitary doses containing from 10 to 80 mg of active principle.

6. A composition according to claim 5, wherein the unitary dose is comprised between 15 and 40 mg.

7. A method for the treatment of digestive diseases comprising administering to a subject in need thereof a therapeutically effective amount of the monohydrated sodium salt of S-tenatoprazole substantially free from the (+) enantiomer or R-tenatoprazole wherein digestive diseases are selected from gastro-oesophageal reflux disease and digestive bleeding in polymedicamented patients.

8. A pharmaceutical composition according to claim 4, wherein the pharmaceutical composition exhibits improved pharmacokinetic properties.

9. A method of preparation of the monohydrated sodium salt of S-tenatoprazole according to claim 1, wherein sodium hydroxide is caused to react on S-tenatoprazole at a temperature between 50 and 700° C., and the salt obtained is precipitated after elimination of the solvent.

10. A method according to claim 9, wherein the reaction temperature is about 600° C.

11. A method according to claim 9, wherein the reaction is conducted in a solvent selected from the group consisting of water, chloroform, DMSO, methanol, and ethanol.

12. An enantioselective method of preparation of the monohydrated sodium salt of S-tenatoprazole, wherein an enantioselective oxidation is conducted on a sulphide of the following general formulation (I)

$$A-CH_2-S-B \quad (I)$$

where A is a 4-methoxy-3,5-dimethyl-2-pyridyl group and B represents a 5-methoxy-imidazo[4, 5-b]pyridyl group, using an oxidising agent in the presence of a vanadium based catalyst and a chiral ligand in a specific sulphide solvent and a specific ligand solvent, followed by salification by sodium hydroxide, in order to obtain the monohydrated sodium salt of S-tenatoprazole.

13. A composition for oral administration of the monohydrated sodium salt of S-tenatoprazole according to claim 1, comprising a mixture of a diluent, a disintegrating agent and the monohydrated sodium salt of S-tenatoprazole, being covered with an enteric film.

14. A composition according to claim 13, wherein the diluent is a cellulosic diluent.

15. A composition according to claim 14, wherein the diluent is an excipient for direct compression.

16. A composition according to claim 13, wherein the disintegrating agent is a cellulosic polymer.

17. A composition according to claim 16, wherein the disintegrating agent is sodium croscarmellose.

18. A composition according to claim 16, wherein the cellulosic polymer is a cellulose carboxymethyl polymer.

* * * * *